United States Patent
Maskara et al.

(10) Patent No.: US 9,681,817 B2
(45) Date of Patent: Jun. 20, 2017

(54) SUPPRESSION OF GLOBAL ACTIVATION SIGNALS DURING ANATOMICAL MAPPING

(71) Applicant: Boston Scientific Scimed, Inc., Maple Grove, MN (US)

(72) Inventors: Barun Maskara, Blaine, MN (US); Shantha Arcot-Krishnamurthy, Renton, WA (US); Pramodsingh H. Thakur, Woodbury, MN (US); Allan C. Shuros, St. Paul, MN (US); Sunipa Saha, Shoreview, MN (US); Shibaji Shome, Arden Hills, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 84 days.

(21) Appl. No.: 14/134,414

(22) Filed: Dec. 19, 2013

(65) Prior Publication Data
US 2014/0180151 A1    Jun. 26, 2014

Related U.S. Application Data

(60) Provisional application No. 61/739,963, filed on Dec. 20, 2012.

(51) Int. Cl.
*A61B 5/044*    (2006.01)
*A61B 5/00*    (2006.01)
(Continued)

(52) U.S. Cl.
CPC ............ *A61B 5/044* (2013.01); *A61B 5/0422* (2013.01); *A61B 5/6858* (2013.01);
(Continued)

(58) Field of Classification Search
CPC ..... A61B 5/0422; A61B 5/044; A61B 5/6858; A61B 5/7203; A61B 18/1492;
(Continued)

(56) References Cited

U.S. PATENT DOCUMENTS

| | | | |
|---|---|---|---|
| 4,407,296 A | 10/1983 | Anderson | |
| 4,962,767 A | 10/1990 | Brownlee | |

(Continued)

FOREIGN PATENT DOCUMENTS

| | | | |
|---|---|---|---|
| CN | 1253761 A | 5/2000 | |
| CN | 200960161 Y | 10/2007 | |

(Continued)

OTHER PUBLICATIONS

International Preliminary Report on Patentability issued in PCT/US2015/031787, mailed Dec. 15, 2016, 8 pages.
(Continued)

*Primary Examiner* — Joseph Dietrich
(74) *Attorney, Agent, or Firm* — Faegre Baker Daniels LLP

(57) ABSTRACT

A method for mapping an anatomical structure includes sensing activation signals of intrinsic physiological activity with a plurality of electrodes disposed in or near the anatomical structure, identifying at least one of the electrodes not in direct contact with the anatomical structure, and adjusting the activation signals sensed by each of the plurality of electrodes based on the activation signals sensed by the identified at least one of the electrodes not in direct contact with the anatomical structure.

11 Claims, 3 Drawing Sheets

(51) Int. Cl.
*A61B 5/042* (2006.01)
*A61B 18/14* (2006.01)
*A61B 17/00* (2006.01)
*A61B 18/00* (2006.01)

(52) U.S. Cl.
CPC ........ *A61B 5/7203* (2013.01); *A61B 18/1492* (2013.01); *A61B 2017/00044* (2013.01); *A61B 2017/00048* (2013.01); *A61B 2017/00053* (2013.01); *A61B 2018/00666* (2013.01); *A61B 2018/00839* (2013.01)

(58) Field of Classification Search
CPC   A61B 2017/00053; A61B 2017/00048; A61B 2017/00044; A61B 2018/00666
See application file for complete search history.

(56) References Cited

U.S. PATENT DOCUMENTS

| | | | |
|---|---|---|---|
| 5,161,539 A | 11/1992 | Evans et al. | |
| 5,647,870 A | 7/1997 | Kordis et al. | |
| 5,683,425 A | 11/1997 | Hauptmann | |
| 5,772,693 A | 6/1998 | Brownlee | |
| 5,776,072 A | 7/1998 | Hsu et al. | |
| 5,782,898 A | 7/1998 | Dahl et al. | |
| 5,817,133 A * | 10/1998 | Houben | A61N 1/3704 607/9 |
| 6,070,094 A | 5/2000 | Swanson et al. | |
| 6,214,025 B1 | 4/2001 | Thistle et al. | |
| 6,233,491 B1 | 5/2001 | Kordis et al. | |
| 6,236,883 B1 | 5/2001 | Ciaccio et al. | |
| 6,400,981 B1 * | 6/2002 | Govari | A61B 5/0422 600/509 |
| 6,650,931 B1 | 11/2003 | McClure et al. | |
| 6,660,021 B1 | 12/2003 | Palmer et al. | |
| 6,735,465 B2 | 5/2004 | Panescu | |
| 6,810,283 B2 * | 10/2004 | Suribhotla | A61N 1/3702 600/509 |
| 7,338,512 B2 | 3/2008 | McGuckin, Jr. et al. | |
| 7,672,722 B1 | 3/2010 | Mengotto | |
| 7,780,694 B2 | 8/2010 | Palmer et al. | |
| 7,850,708 B2 | 12/2010 | Pal | |
| 7,933,643 B1 | 4/2011 | Gill et al. | |
| 8,019,409 B2 | 9/2011 | Rosenberg et al. | |
| 8,055,333 B2 | 11/2011 | Duann et al. | |
| 8,060,202 B2 | 11/2011 | Betzold et al. | |
| 8,090,434 B2 | 1/2012 | Lian et al. | |
| 8,155,739 B2 | 4/2012 | Keel et al. | |
| 8,165,666 B1 | 4/2012 | Briggs et al. | |
| 8,175,693 B2 | 5/2012 | Rosenberg et al. | |
| 8,195,292 B2 | 6/2012 | Rosenberg et al. | |
| 8,543,195 B1 | 9/2013 | Brockway et al. | |
| 9,131,866 B2 | 9/2015 | Thakur et al. | |
| 2003/0236466 A1 | 12/2003 | Tarjan et al. | |
| 2004/0039293 A1 | 2/2004 | Porath et al. | |
| 2004/0176694 A1 | 9/2004 | Kim et al. | |
| 2005/0154321 A1 | 7/2005 | Wolinsky et al. | |
| 2005/0209678 A1 | 9/2005 | Henkes et al. | |
| 2005/0288600 A1 | 12/2005 | Zhang et al. | |
| 2006/0069322 A1 | 3/2006 | Zhang et al. | |
| 2006/0116595 A1 | 6/2006 | Palreddy et al. | |
| 2006/0253044 A1 | 11/2006 | Zhang et al. | |
| 2008/0071182 A1 | 3/2008 | Cazares et al. | |
| 2008/0109041 A1 | 5/2008 | de Voir | |
| 2008/0194979 A1 | 8/2008 | Madry et al. | |
| 2008/0243214 A1 | 10/2008 | Koblish | |
| 2008/0281369 A1 | 11/2008 | KenKnight et al. | |
| 2009/0240157 A1 | 9/2009 | Lian et al. | |
| 2009/0254140 A1 | 10/2009 | Rosenberg et al. | |
| 2009/0306732 A1 | 12/2009 | Rosenberg et al. | |
| 2009/0318995 A1 | 12/2009 | Keel et al. | |
| 2010/0152801 A1 | 6/2010 | Koh et al. | |
| 2010/0256699 A1 | 10/2010 | Makdissi | |
| 2010/0268059 A1 | 10/2010 | Ryu et al. | |
| 2011/0054559 A1 | 3/2011 | Rosenberg et al. | |
| 2011/0054560 A1 | 3/2011 | Rosenberg et al. | |
| 2011/0066201 A1 | 3/2011 | Rosenberg et al. | |
| 2011/0066202 A1 | 3/2011 | Rosenberg et al. | |
| 2011/0066203 A1 | 3/2011 | Rosenberg et al. | |
| 2011/0092809 A1 | 4/2011 | Nguyen et al. | |
| 2011/0118803 A1 | 5/2011 | Hou et al. | |
| 2011/0144510 A1 | 6/2011 | Ryu et al. | |
| 2011/0184274 A1 | 7/2011 | Rosenberg et al. | |
| 2011/0213260 A1 | 9/2011 | Keel et al. | |
| 2011/0251505 A1 | 10/2011 | Narayan et al. | |
| 2011/0295137 A1 | 12/2011 | Rosenberg et al. | |
| 2011/0319954 A1 | 12/2011 | Niazi et al. | |
| 2012/0157865 A1 | 6/2012 | Stein et al. | |
| 2012/0184863 A1 | 7/2012 | Harlev et al. | |
| 2012/0327204 A1 | 12/2012 | Friedman et al. | |
| 2013/0274582 A1 * | 10/2013 | Afonso | A61B 5/0422 600/374 |
| 2013/0345537 A1 | 12/2013 | Thakur et al. | |
| 2013/0345577 A1 | 12/2013 | Thakur et al. | |
| 2013/0345583 A1 | 12/2013 | Thakur et al. | |
| 2014/0018792 A1 | 1/2014 | Gang et al. | |
| 2014/0067279 A1 | 3/2014 | George et al. | |
| 2014/0081114 A1 | 3/2014 | Shachar et al. | |
| 2014/0187991 A1 | 7/2014 | Thakur et al. | |
| 2014/0316294 A1 | 10/2014 | Maskara et al. | |
| 2015/0257671 A1 | 9/2015 | Laughner et al. | |
| 2015/0342536 A1 | 12/2015 | Kovtun et al. | |

FOREIGN PATENT DOCUMENTS

| | | |
|---|---|---|
| CN | 101365379 A | 2/2009 |
| CN | 101558993 A | 10/2009 |
| EP | 1543865 A1 | 6/2005 |
| EP | 2863792 A1 | 4/2015 |
| EP | 2863793 A1 | 4/2015 |
| JP | H11511666 A | 10/1999 |
| JP | 2005501674 A | 1/2005 |
| JP | 2006025836 A | 2/2006 |
| JP | 2013523344 A | 6/2013 |
| JP | 2014502556 A | 2/2014 |
| WO | WO0045700 A1 | 8/2000 |
| WO | WO0047278 A1 | 8/2000 |
| WO | WO2011041489 A2 | 4/2001 |
| WO | WO03022356 A2 | 3/2003 |
| WO | WO2006037172 A1 | 4/2006 |
| WO | WO2008118992 A1 | 10/2008 |
| WO | WO2011075328 A1 | 6/2011 |
| WO | 2014058484 A1 | 4/2014 |
| WO | 2015187371 A1 | 12/2015 |

OTHER PUBLICATIONS

International Preliminary Report on Patentability issued in PCT/US2013/076958, mailed Jun. 30, 2015, 8 pages.
International Search Report and Written Opinion issued in International Application No. PCT/US2013/046843, mailed Oct. 23, 2013, 12 pages.
International Search Report and Written Opinion issued in PCT/US2013/046841, mailed Oct. 15, 2013, 12 pages.
International Search Report and Written Opinion issued in PCT/US2013/076958, mailed Apr. 7, 2014, 14 pages.
International Search Report and Written Opinion issued in PCT/US2015/031787, mailed Aug. 5, 2015, 11 pages.
Potter, M. et al., "Competing ICA Techniques in Biomedical Signal Analysis", Electrical and Computer Engineering, 2001, Canadian Conference on May 13-16, 2001, Piscataway, NJ, USA, IEEE, vol. 2, May 13, 2001, pp. 987-992.
Zhou, Yu et al., "A New United Analysis Method for Epicardial Mapping Signals", Bioinformatics and Biomedical Engineering, 2008, ICBBE 2008, The Second International Conference, IEEE, Piscataway; NJ, USA, May 16, 2008, pp. 636-639.

* cited by examiner

SUPPRESSION OF GLOBAL ACTIVATION SIGNALS DURING ANATOMICAL MAPPING

CROSS-REFERENCE TO RELATED APPLICATIONS

This application claims the benefit under 35 U.S.C. §119(e) to U.S. Provisional Application 61/739,963, entitled "SUPPRESSION OF GLOBAL ACTIVATION SIGNALS DURING ANATOMICAL MAPPING, filed on Dec. 20, 2012, which is herein incorporated by reference in its entirety.

TECHNICAL FIELD

The present disclosure relates to cardiac mapping systems. More specifically, the present disclosure relates to a cardiac mapping system configured to suppress far-field activation during mapping based on activation signals sensed by non-contact electrodes.

BACKGROUND

Diagnosing and treating heart rhythm disorders often involve the introduction of a catheter having a plurality of sensors/probes into a cardiac chamber through the surrounding vasculature. The sensors detect electric activity of the heart at sensor locations in the heart. The electric activity is generally processing into electrogram signals that represent signal propagation through cardiac tissue at the sensor locations.

The sensors in cardiac chamber may detect far-field electrical activity, i.e. the ambient electrical activity away from the sensors, which can negatively affect the detection of local electrical activity, signals at or near the sensor location. For example, ventricular activation may present itself as far-field signals substantially simultaneously on multiple sensors situated in the atrium. Due to the magnitude of ventricular activations, the phenomenon can mask significant aspects of highly localized activity and thus portray inaccurate activation maps and/or reduced resolution activation maps upon which physicians rely to administer therapy, e.g. ablation therapy, to a patient.

SUMMARY

In Example 1, a method for mapping an anatomical structure includes sensing activation signals of intrinsic physiological activity with a plurality of electrodes disposed in or near the anatomical structure, identifying at least one of the electrodes not in direct contact with the anatomical structure, and adjusting the activation signals sensed by each of the plurality of electrodes based on the activation signals sensed by the identified at least one of the electrodes not in direct contact with the anatomical structure.

In Example 2, the method according to Example 1, wherein the step of identifying at least one of the electrodes not in direct contact with the anatomical structure includes determining a maximum amplitude of the activation signals sensed by each of the electrodes, and identifying one or more electrodes having sensed activation signals with a lowest maximum amplitude.

In Example 3, the method according to either one of Examples 1 and 2, wherein the adjusting step includes filtering the sensed activation signals with the lowest maximum amplitude from the activation signals sensed by each of the electrodes.

In Example 4, the method according to any one of Examples 1-3, wherein the adjusting step includes setting a signal floor based on the local activation signals sensed by the identified at least one of the electrodes.

In Example 5, the method according to any one of Examples 1-4 further including generating a map of the anatomical structure based on the adjusted activation signals.

In Example 6, a method for mapping an anatomical structure includes sensing activation signals of intrinsic physiological activity with a plurality of electrodes disposed in or near the anatomical structure, determining a maximum amplitude of the activation signals sensed by each of the electrodes, identifying one or more electrodes having activation signals with a lowest maximum amplitude, filtering the activation signals with the lowest maximum amplitude from the activation signals sensed by each of the electrodes, and generating a map of the anatomical structure based on the filtered activation signals.

In Example 7, the method according to Example 6, wherein the filtering step includes subtracting the activations determined from the lowest maximum amplitude signals from the activation signals sensed by each of the electrodes.

In Example 8, the method according to either one of Examples 6 and 7, wherein the filtering step includes determining a dynamic threshold floor based on the lowest maximum amplitude signals and applying a dynamic thresholding algorithm to the activation signals based on the dynamic threshold floor.

In Example 9, the method according to any one of Examples 6-8 further including displaying the map of the anatomical structure.

In Example 10, an anatomical mapping system includes a plurality of mapping electrodes each having an electrode location and channel and configured to detect activation signals of intrinsic physiological activity within an anatomical structure. A processor system is associated with the plurality of mapping electrodes. The processor system is configured to record the detected activation signals and associate one of the plurality of mapping electrodes with each recorded activation signal. The processor system is further configured to identify at least one mapping electrode not in direct contact with the anatomical structure, determine a global activation signal from the identified at least one mapping electrode, and determine local activation signals from the recorded activation signals based on the determined global activation signal.

In Example 11, the anatomical mapping system according to Example 10, wherein the processor system is further configured to generate an activation map of the local activation signals.

In Example 12, the anatomical mapping system according to either of Examples 10 or 11, and further comprising a display configured to display a map of the anatomical structure.

In Example 13, the anatomical mapping system according Example 12, wherein the display is configured to display the activation map of the local activation signals.

In Example 14, the anatomical mapping system according to any one of Examples 10-13, wherein, to determine the global activation signal, the processing system is further configured to determine a maximum amplitude of the recorded activation signals for each electrode channel and identify one or more mapping electrodes having a lowest maximum amplitude.

In Example 15, the anatomical mapping system according to any one of Examples 10-14, wherein the processing system is configured to apply a dynamic threshold determination algorithm to the activation signals based on the determined global activation signal.

In Example 16, the anatomical mapping system according to any one of Examples 10-15, wherein the processing system is further configured to set a signal floor based on the local activation signals sensed by the identified at least one of the electrodes.

In Example 17, the anatomical mapping system according to any one of Examples 10-16, wherein to determine the local activation signal, the processing system is further configured to filter the global activation signal from the detected activation signals.

In Example 18, the anatomical mapping system according to anyone of Examples 10-17, wherein the processing system is further configured to subtract the global activation signal from the activation signals sensed by each of the plurality of mapping electrodes.

In Example 19, the anatomical mapping system according to any of Examples 10-18, further comprising a catheter having a flexible body and a three-dimensional electrode structure coupled to the flexible body, wherein the plurality of mapping electrodes are disposed on the three-dimensional electrode structure.

In Example 20, the anatomical mapping system according to any of Examples 10-19, wherein the three-dimensional electrode structure is configured to transition between collapsed and expanded configurations.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
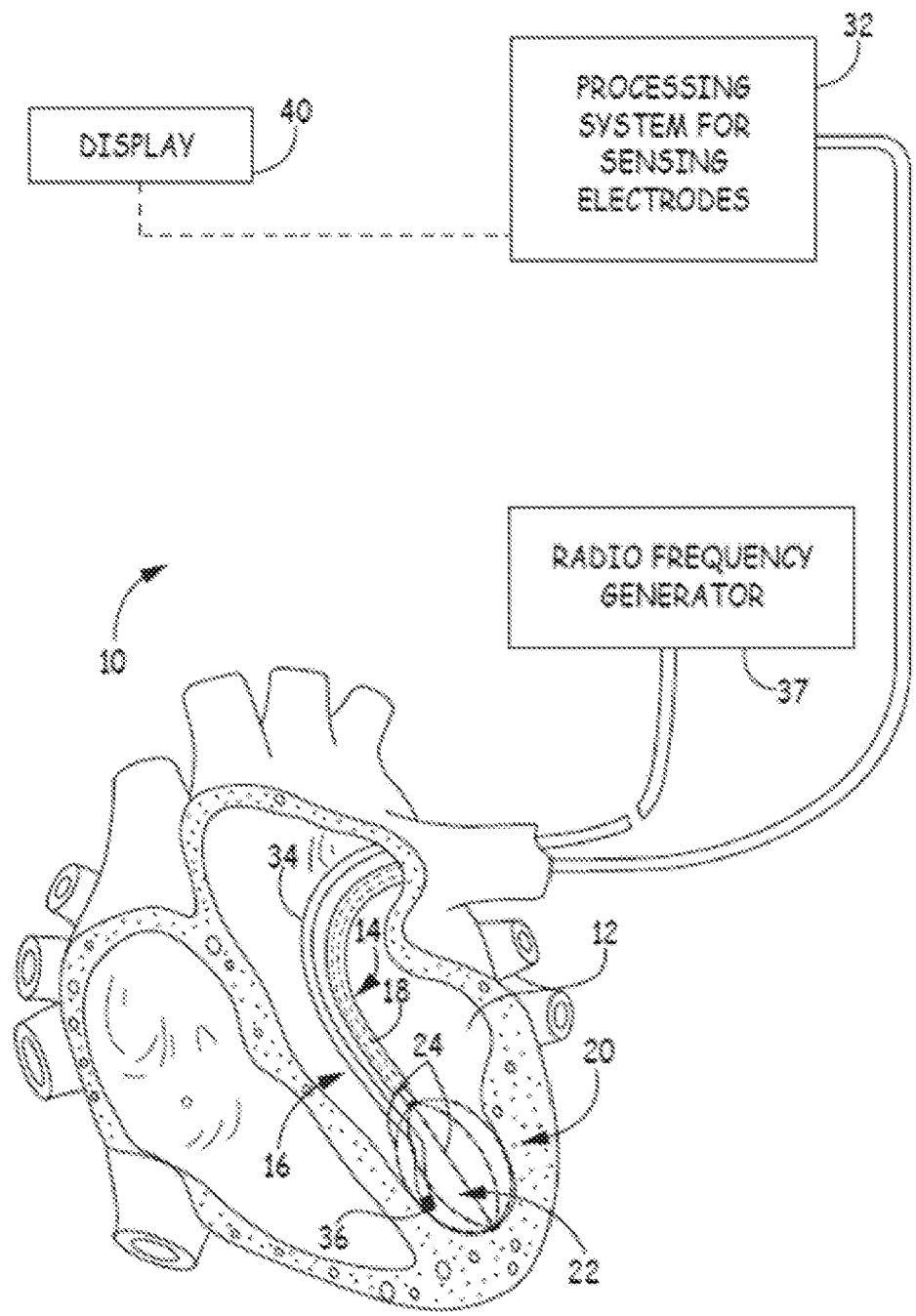
FIG. 1 a schematic view of an embodiment of a catheter system for accessing a targeted tissue region in the body for diagnostic and therapeutic purposes.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a system 10 for accessing a targeted tissue region in the body for diagnostic or therapeutic purposes. FIG. 1 generally shows the system 10 deployed in the left ventricle of the heart. Alternatively, system 10 can be deployed in other regions of the heart, such as the left atrium, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, and other regions of the body, including in systems that are not necessarily catheter-based.

The system 10 includes a mapping probe 14 and an ablation probe 16. In FIG. 1, each is separately introduced into the selected heart region 12 through a vein or artery (e.g., the femoral vein or artery) through suitable percutaneous access. Alternatively, the mapping probe 14 and ablation probe 16 can be assembled in an integrated structure for simultaneous introduction and deployment in the heart region 12.

The mapping probe 14 has a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used wherein the geometry of the electrode structure and electrode locations are known. The multiple electrode structure 20 carries a plurality of mapping electrodes 24 each having an electrode location and channel. Each electrode 24 is configured to sense intrinsic physiological activity in the anatomical region on which the ablation procedure is to be performed. In some embodiments, the electrodes are configured to detect activation signals of the intrinsic physiological activity within the anatomical structure, e.g., the activation times of cardiac activity.

The electrodes 24 are electrically coupled to a processing system 32. A signal wire (not shown) is electrically coupled to each electrode 24 on the basket structure 20. The wires extend through the body 18 of the probe 14 and electrically couple each electrode 24 to an input of the processing system 32, as will be described later in greater detail. The electrodes 24 sense intrinsic electrical activity in the anatomical region, e.g., myocardial tissue. The sensed activity, e.g. activation signals, is processed by the processing system 32 to assist the physician by generating an anatomical map, e.g. action potential duration (APD) map or an activation map, to identify the site or sites within the heart appropriate for ablation. The processing system 32 identifies a near-field signal component, i.e. activation signals associated with local activation and originating from the tissue adjacent to the mapping electrode 24, from an obstructive far-field signal component, i.e. activation signals originating from non-adjacent tissue, within the sensed activation signals. For example, in an atrial study, the near-field signal component includes activation signals originating from atrial myocardial tissue whereas far-field signal component includes activation signals original from the ventricular myocardial tissue. The near-field activation signal component can be further analyzed to find the presence of a pathology and to determine a location suitable for ablation for treatment of the pathology, e.g. ablation therapy.

In some embodiments, the processing system 32 may be configured to measure the intrinsic electrical activity in the myocardial tissue adjacent to the electrodes 24. For example, in some embodiments, the processing system 32 is configured to detect intrinsic electrical activity associated with a dominant rotor in the anatomical feature being mapped. Studies have shown that dominant rotors have a role in the initiation and maintenance of atrial fibrillation, and ablation of the rotor path and/or rotor core may be effective in terminating the atrial fibrillation. In either situation, the processing system 32 processes the sensed activation signals to isolate the near-field signal component and generate an APD map based on the isolated near-field signal component. The APD map may be used by the physician to identify a site suitable for ablation therapy.

The ablation probe 16 includes a flexible catheter body 34 that carries one or more ablation electrodes 36. The one or more ablation electrodes 36 are electrically connected to a radio frequency generator (RF) 37 that is configured to deliver ablation energy to the one or more ablation electrodes 36. The ablation probe 16 is movable with respect to the anatomical feature to be treated, as well as the structure 20. The ablation probe 16 is positionable between or adjacent to electrodes 24 of the structure 20 as the one or more ablation electrodes 36 are positioned with respect to the tissue to be treated.

The processing system 32 outputs to a display 40 the generated APD map to the physician. In the illustrated embodiment, the processing system 32 includes an output display device 40 (e.g., a CRT, LED display, or a printer). The device 40 presents the APD map in a format most useful to the physician. In addition, the processing system 32 may generate position-identifying output for display on the display device 40 that aids the physician in guiding the ablation electrode(s) 36 into contact with tissue at the site identified for ablation.

Figure 2:
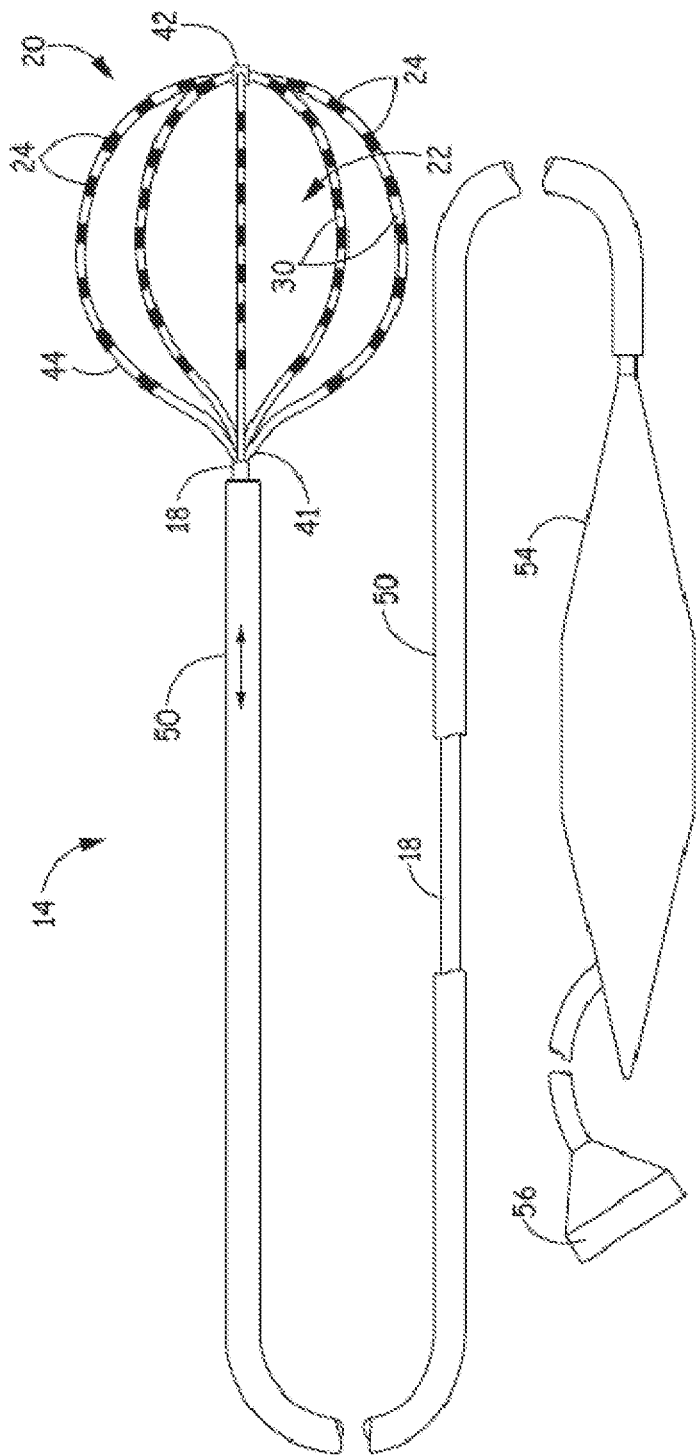
FIG. 2 is a schematic view of an embodiment of a mapping catheter having a basket functional element carrying structure for use in association with the system of FIG. 1.

FIG. 2 illustrates an embodiment of the mapping catheter 14 including electrodes 24 at the distal end suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity, e.g. activation signals, in the myocardial tissue, the sensed activity is then processed by the processing system 32 to assist the physician in identifying the site or sites having a heart rhythm disorder or other myocardial pathology via a generated and displayed APD map. This process is commonly referred to as mapping. This information can then be used to determine an appropriate location for applying appropriate therapy, such as ablation, to the identified sites, and to navigate the one or more ablation electrodes 36 to the identified sites.

The illustrated three-dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is larger (e.g., 40 mm in diameter or greater).

A slidable sheath 50 is movable along the major axis of the catheter body 30. Moving the sheath 50 forward (i.e., toward the distal end) causes the sheath 50 to move over the three dimensional structure 20, thereby collapsing the structure 20 into a compact, low profile condition suitable for introduction into an interior space, such as, for example, into the heart. In contrast, moving the sheath 50 rearward (i.e., toward the proximal end) exposes the three dimensional structure 20, allowing the structure 20 to elastically expand and assume the pretensed position illustrated in FIG. 2. Further details of embodiments of the three dimensional structure 20 are disclosed in U.S. Pat. No. 5,647,870, entitled "Multiple Electrode Support Structures," which is hereby incorporated by reference in its entirety.

A signal wire (not shown) is electrically coupled to each mapping electrode 26. The wires extend through the body 30 of the mapping catheter 20 into a handle 54, in which they are coupled to an external connector 56, which may be a multiple pin connector. The connector 56 electrically couples the mapping electrodes 24 to the processing system 32. Further details on mapping systems and methods for processing signal generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are incorporated herein by reference.

It is noted that other multi-electrode structures could be deployed on the distal end of the mapping catheter 14. It is further noted that the multiple mapping electrodes 24 may be disposed on more than one structure rather than, for example, the single mapping catheter 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Although the mapping electrodes 24 have been described as being carried by dedicated mapping probes, such as the mapping catheter 14, the mapping electrodes may be carried on non-mapping dedicated probes or multifunction probes. For example, an ablation catheter, such as the ablation catheter 16, can be configured to include one or more mapping electrodes 24 disposed on the distal end of the catheter body and coupled to the signal processing system 32 and guidance system 38. As another example, the ablation electrode at the distal end of the ablation catheter may be coupled to the signal processing system 32 to also operate as a mapping electrode.

Figure 3:
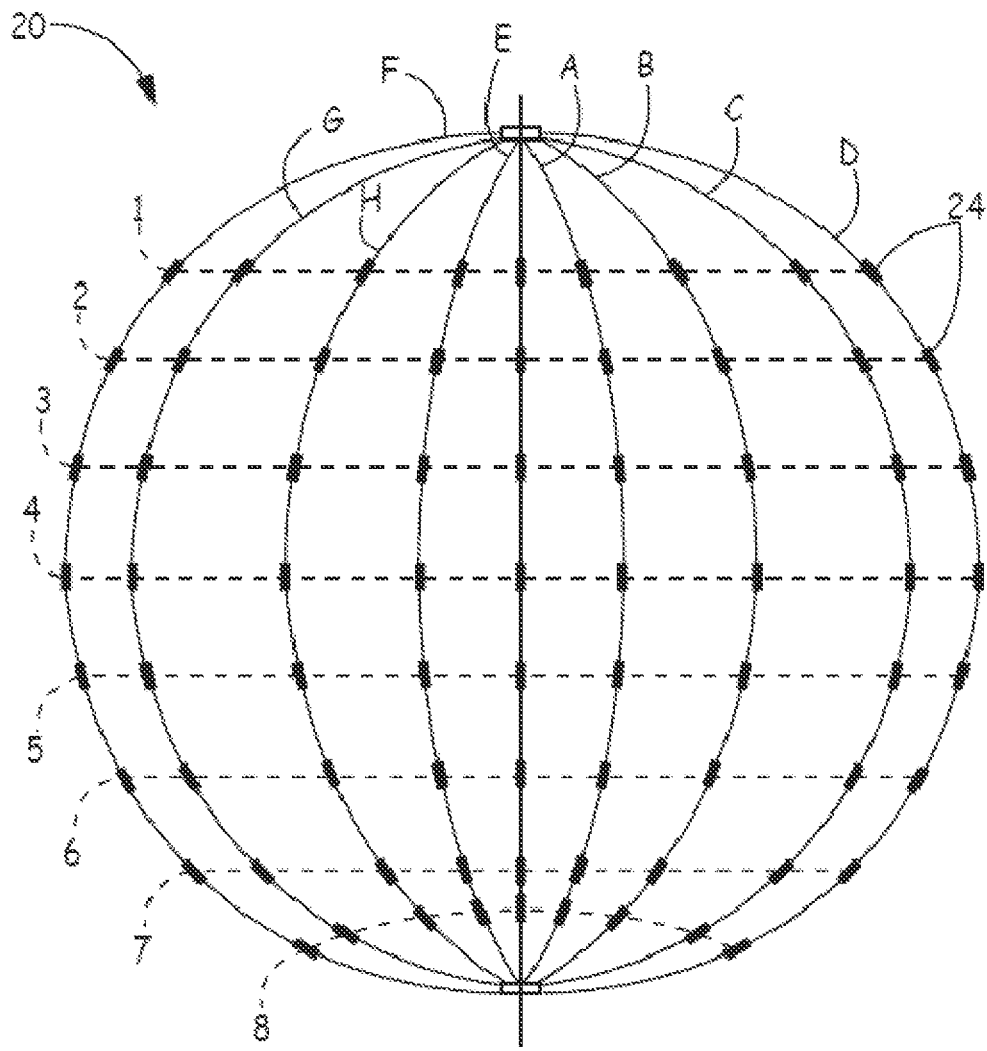
FIG. 3 is a schematic side view of an embodiment of the basket functional element including a plurality of mapping electrodes.

To illustrate the operation of the system 10, FIG. 3 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on a basket structure 20, the mapping electrodes 24 may alternatively be arranged in different numbers, on different structures, and/or in different positions. In addition, multiple basket structures can be deployed in the same or different anatomical structures to simultaneously obtain signals from different anatomical structures.

After the basket structure 20 is positioned adjacent to the anatomical structure to be treated (e.g., left atrium or left ventricle of the heart), the processing system 32 is configured to record the activation signals from each electrode 24 channel related to intrinsic physiological activity of the anatomical structure, i.e. the electrodes 24 measure electrical activation signals intrinsic to the physiology of the anatomical structure. The processing system is further configured to identify at least one mapping electrode not in direct contact or with the anatomical structure. Based on the activation signals recorded by the identified at least one non-contact mapping electrode 24, the processing system 32 determines a global activation signal and a local activation signal. In some embodiments, activation maps are then generated based on the local activation signals.

To determine locations of the at least one non-contact mapping electrode, the processing system 32 is configured to determine the maximum amplitude of the activation signals sensed by each of the mapping electrodes 24. The electrode 24 channels with the lowest maximum amplitude are likely not to be in direct contact with the anatomical structure that is being studied. The activation signals detected by the identified non-contact mapping electrodes correspond with far-field activation signals, i.e. global activation signals, which are detrimental to the sensing of the local activation signal, i.e. near-field signal component. The maximum amplitude of the signal from these electrodes corresponds to the far-field signal, and hence can be used to set the dynamic threshold for all the channels to avoid sensing far field signals.

To determine the global or far-field activation signal, the processing system 32 is configured to determine a dynamic threshold floor according to the activation signals recorded by the identified non-contact mapping electrodes 24, i.e. the determined lowest maximum amplitude. The processing system 32 is configured to apply a dynamic thresholding algorithm on the sensed activation signals based on the dynamic threshold floor to determine the global activation signal for each electrode 24. The dynamic thresholding algorithm segments the recorded activation signals based on a correlation between an amplitude and the determined dynamic threshold floor. Those activation signals with amplitudes at or below the dynamic threshold floor, i.e. those activation signals corresponding to global or fair-field activation signals, are classified or identified as global activation signals. Whereas, the activation signals with amplitudes above the dynamic threshold floor, i.e. local or near-field activation signals, are classified or identified as local activation signals. The dynamic threshold floor corresponds to the amplitude of the global or far-field activation signal and provides a metric for identifying activation signals with the same or similar amplitude to isolate local activity from global activity.

To determine the local or near-field activation signal, the processing system 32 is configured to filter the determined global activation signal from the activation signal sensed by each mapping electrode 24. For example, in some embodiments, the processing system 32 subtracts the global activation signal from the activation signal sensed by each mapping electrode 24. In some embodiments, the signal processing 32 then generates a map of the anatomical structure according to the determined local activation signal. The map may then be displayed on the display device 40 for a physician or clinician to examine.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof

We claim:

1. An anatomical mapping system comprising:
   a plurality of mapping electrodes configured to detect activation signals of intrinsic physiological activity within an anatomical structure, each of the plurality of mapping electrodes having an electrode location and channel;
   a processing system associated with the plurality of mapping electrodes, wherein the processing system is configured to record the detected activation signals and associate one of the plurality of mapping electrodes with each recorded activation signal, and wherein the processing system is further configured to:
   identify at least one mapping electrode not in direct contact with the anatomical structure,
   determine a far-field activation signal from the identified at least one mapping electrode by determining a lowest maximum amplitude of the recorded activation signals of the identified at least one mapping electrode,
   determine near-field activation signals from the recorded activation signals based on the determined far-field activation signal, and
   generate an activation map of the near-field activation signals; and
   a display configured to display the activation map of the near-field activation signals.

2. The anatomical mapping system according to claim 1, wherein the display is configured to display a map of the anatomical structure.

3. The anatomical mapping system according to claim 1, wherein the processing system is further configured to determine a dynamic threshold floor based on the activation signals sensed by the identified at least one of the electrodes.

4. The anatomical mapping system according to claim 3, wherein the processing system is configured to apply a dynamic thresholding algorithm to the activation signals based on the determined dynamic threshold floor.

5. The anatomical mapping system according to claim 1, wherein to determine the near-field activation signal, the processing system is further configured to filter the far-field activation signal from the detected activation signals.

6. The anatomical mapping system according to claim 1, wherein the processing system is further configured to subtract the far-field activation signal from the activation signals sensed by each of the plurality of mapping electrodes.

7. The anatomical mapping system according to claim 1, further comprising a catheter having a flexible body and a three-dimensional electrode structure coupled to the flexible body, wherein the plurality of mapping electrodes are disposed on the three-dimensional electrode structure.

8. The anatomical mapping system according to claim 7, wherein the three-dimensional electrode structure is configured to transition between collapsed and expanded configurations.

9. An anatomical mapping system comprising:
   a plurality of mapping electrodes configured to detect activation signals of intrinsic physiological activity within an anatomical structure, each of the plurality of mapping electrodes having an electrode location and channel;

a processing system associated with the plurality of mapping electrodes, wherein the processing system is configured to record the detected activation signals and associate one of the plurality of mapping electrodes with each recorded activation signal, and wherein the processing system is further configured to:
- identify at least one mapping electrode not in direct contact with the anatomical structure,
- determine a far-field activation signal from the identified at least one mapping electrode, and
- filter the far-field activation signals from the detected activation signals to determine near-field activation signals from the recorded activation signals; and a display configured to display an activation map of the near-field activation signals.

10. The anatomical mapping system according to claim 9, wherein the processing system is further configured to subtract the far-field activation signal from the activation signals sensed by each of the plurality of mapping electrodes.

11. The anatomical mapping system according to claim 9, wherein the processing system is configured to identify at least one mapping electrode not in direct contact with the anatomical structure by:
- determining a maximum amplitude of the activation signals sensed by each of the electrodes, and
- identifying one or more electrodes having sensed activation signals with a lowest maximum amplitude.

* * * * *